United States Patent
Bouchama et al.

(10) Patent No.: US 10,188,548 B2
(45) Date of Patent: Jan. 29, 2019

(54) ARTIFICIAL HYPOTHALAMUS FOR BODY TEMPERATURE REGULATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Abderrezak Bouchama, Riyadh (SA); Ali Almuntashri, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 539 days.

(21) Appl. No.: 15/010,737

(22) Filed: Jan. 29, 2016

(65) Prior Publication Data

US 2017/0216086 A1  Aug. 3, 2017

(51) Int. Cl.
| | | |
|---|---|---|
| *A61F 7/00* | (2006.01) | |
| *A61B 5/00* | (2006.01) | |
| *A61B 5/01* | (2006.01) | |
| *A61B 5/026* | (2006.01) | |
| *A61B 5/029* | (2006.01) | |

(Continued)

(52) U.S. Cl.
CPC .................. *A61F 7/00* (2013.01); *A61B 5/00* (2013.01); *A61B 5/01* (2013.01); *A61B 5/026* (2013.01); *A61B 5/029* (2013.01); *A61B 5/0488* (2013.01); *A61B 5/11* (2013.01); *A61F 2007/0086* (2013.01); *A61F 2007/0093* (2013.01);

(Continued)

(58) Field of Classification Search
CPC combination set(s) only.
See application file for complete search history.

(56) References Cited

U.S. PATENT DOCUMENTS

| | | | |
|---|---|---|---|
| 5,441,476 A | 8/1995 | Kitado et al. | |
| 5,796,919 A * | 8/1998 | Kubica | G05B 13/0275 706/1 |

(Continued)

OTHER PUBLICATIONS

Christoph Schär, et al., "Hot news from summer 2003", Nature, vol. 432, Dec. 2004, pp. 559-560.

(Continued)

*Primary Examiner* — Joseph Stoklosa
*Assistant Examiner* — Adam Avigan
(74) *Attorney, Agent, or Firm* — Oblon, McClelland, Maier & Neustadt, L.L.P.

(57) ABSTRACT

An artificial hypothalamus system for regulating body temperature for a human can include monitoring data from a plurality of sensors. The sensor data can be used in a control system to optimize temperature regulation in real time through a feedback loop. The feedback loop can include monitoring the sensor data, evaluating a predetermined set of fuzzy rules using the data, and combining the output of the fuzzy rules to produce a precise value. The precise value can correspond to an output level for various temperature regulation devices, and a signal can be transmitted based on the precise value to activate the temperature regulation devices to a corresponding level of output.

20 Claims, 9 Drawing Sheets

(51) Int. Cl.
  *A61B 5/0488* (2006.01)
  *A61B 5/11* (2006.01)
(52) U.S. Cl.
  CPC ............... *A61F 2007/0094* (2013.01); *A61F 2007/0096* (2013.01)

(56) References Cited

U.S. PATENT DOCUMENTS

| | | | | |
|---|---|---|---|---|
| 5,817,003 | A * | 10/1998 | Moll | A61G 11/00 600/22 |
| 9,314,367 | B2 * | 4/2016 | Callister | A61F 7/0085 |
| 2009/0131835 | A1 * | 5/2009 | Voorhees | A61B 5/01 600/595 |
| 2009/0312676 | A1 * | 12/2009 | Rousso | A61F 7/10 601/15 |
| 2010/0087900 | A1 * | 4/2010 | Flint | A61B 5/1101 607/104 |
| 2011/0041246 | A1 | 2/2011 | Li et al. | |
| 2014/0148706 | A1 * | 5/2014 | Van Treeck | A61B 5/015 600/474 |
| 2014/0277308 | A1 * | 9/2014 | Cronise | A61F 7/00 607/112 |

OTHER PUBLICATIONS

Cornelia W. Hoedemaekers, et al. "Comparison of cooling methods to induce and maintain normo- and hypothermia in intensive care unit patients: a prospective intervention study", Critical Care, vol. 11, No. 4, Aug. 2007, 6 pages.

Abderrezak Bouchama, et al., "Cooling and hemodynamic management in heatstroke: practical recommendations", Critical Care, vol. 11, No. 3, May 2007, pp. 1-10.

Jean-Marie Robine, et al., "Death toll exceeded 70,000 in Europe during the summer of 2003", Comptes Rendus Biologies, vol. 331, No. 2, Feb. 2008, 2 pages.

Abderrezak Bouchama, et al., "Heat Stroke", N Engl J Med, vol. 346, No. 25, Jun. 2002, 2 pages.

Jan C. Semenza, et al., "Heat-Related Deaths During the Jul. 1995 Heat Wave in Chicago", the New England Journal of Medicine, vol. 335, No. 2, Jul. 1996, pp. 84-90.

T. Stephen Jones, et al., "Morbidity and Mortality Associated With the Jul. 1980 Heat Wave in St. Louis and Kansas City, Mo.", JAMA, vol. 247, No. 24, Jun. 1982, 3 pages (Abstract only).

Stephen A. Bernard, et al., "Treatment of Comatose Survivors of Out-of-Hospital Cardiac Arrest with Induced Hypothermia", the New England Journal of Medicine, vol. 346, No. 8, Feb. 2002, pp. 557- 563.

* cited by examiner

ARTIFICIAL HYPOTHALAMUS FOR BODY TEMPERATURE REGULATION

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Thermoregulation in humans includes a temperature range for a core temperature, where the core comprises internal organs (including the brain), and a specific temperature range for a shell, where the shell comprises skin and extremeties (hands, legs, nose, ears, etc.).

In humans, the hypothalamus regulates the core temperature within a narrow range, approximately 36.1° C. to 37.8° C. (96.98° F. to 100.04° F.). In other words, the hypothalamus functions as a thermostat preset at 37° C., and maintains this core temperature range by constantly regulating production and loss of heat.

Body heat is generated by the catabolism of intracellular proteins, carbohydrates, and fats provided by our nutrition. The body heat can be further increased by increased muscle activity, such as during exercise.

The daily excess heat production is eliminated along a gradient of temperature between core (37° C.), the skin (33° C.) and environment if it is less than 33° C. The heat is transported by the blood to the skin and then dissipated to the environment. The hypothalamus adjusts the heat loss by regulating the skin and the core circulation. For example, if there is excess heat production, the hypothalamus closes (vasoconstriction) the core circulation and opens (vasodilate) the skin circulation, which shifts up to 70% of our cardiac output away from the core organs (except heart and brain). It also increases the cardiac output from 5 liters per min to up to 20 liters per min when exercising in high ambient temperature.

Conversely, in a situation with a low environmental temperature, the skin temperature drops and thermoreceptors on the skin send signals to the hypothalamus, which immediately reacts by insulating the body via closure of the skin circulation. Our extremities (fingers, nose, ears, etc.) may become blue and painful. If this action is not sufficient to maintain the core temperature at 37° C., the hypothalamus triggers muscle shivering which produces heat.

Exposure to a hot environment may result in heatstroke, which is a life-threatening condition characterized by a rapid increase in core temperature, multiple organ dysfunction, and tissue injury. It is a leading cause of mortality and neurological damage when there is an unaccustomed and sustained increase in climatic temperature, such as during a heat wave, and/or any prolonged exposure without proper precautions. Hyperthermia is the primary mechanism of cell death and tissue injury in heatstroke. The severity of injury is a function of the degree of hyperthermia and duration of exposure. An objective in the treatment of hyperthermia is to decrease body temperature as quickly as possible to prevent irreversible damage and death. Cooling techniques can induce severe shivering and skin vasoconstriction, which can increase heat production and decrease heat elimination resulting in the opposite of the desired cooling effect. Also, the rate of cooling can be unpredictable, varying from failure to cool to excessive cooling.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

A system for regulating body temperature for a human can be an artificial hypothalamus. According to one or more embodiments of the disclosed subject matter, the artificial hypothalamus can simultaneously monitor skin temperature, circulation, muscle activity, and the like. The combined signals can allow the artificial hypothalamus react more quickly than the patient's hypothalamus. For example, the artificial hypothalamus can stop rapid cooling and begin warming the skin to maintain skin temperature at 32° C. to 33° C., thereby preventing the patient's thermoreceptors from sending signals to the patient's hypothalamus, which reacts by vasoconstriction and shivering, which stops the cooling effect and increases heat production (i.e., the opposite of the desired cooling). When the skin is warm, the artificial hypothalamus can cause cooling to begin again, thereby creating a warm and cold cycle, which prevents the patient's hypothalamus from reacting negatively. Therefore, cooling can be efficient, predictable, and well tolerated by the patient (e.g., prevent shivering, discomfort, etc.).

The system can include monitoring data from a plurality of sensors. The sensor data can be used in a control system to optimize temperature regulation in real time through a feedback loop. The control system can be, but is not limited to, a Fuzzy Logic-based-system, for example. The feedback loop can include monitoring the sensor data, evaluating a predetermined set of fuzzy rules using the data, and combining the output of the fuzzy rules to produce a precise value. The precise value can correspond to an output level for various temperature regulation devices, and a signal can be transmitted based on the precise value to activate the temperature regulation devices to a corresponding level of output.

The system can maintain optimal cooling by accounting for the human thermoregulatory response mechanisms, such that the optimal cooling can prevent and/or minimize skin vasoconstriction and shivering, while constantly adjusting for the best gradient of temperature to eliminate stored heat, for example.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, terms such as "first," "second," "third," etc., merely identify one of a number of portions, components, points of reference, operations and/or functions as described herein, and likewise do not necessarily limit embodiments of the disclosed subject matter to any particular configuration or orientation.

Referring now to the drawings, wherein like reference numerals designate identical or corresponding parts throughout the several views.

Figure 1:
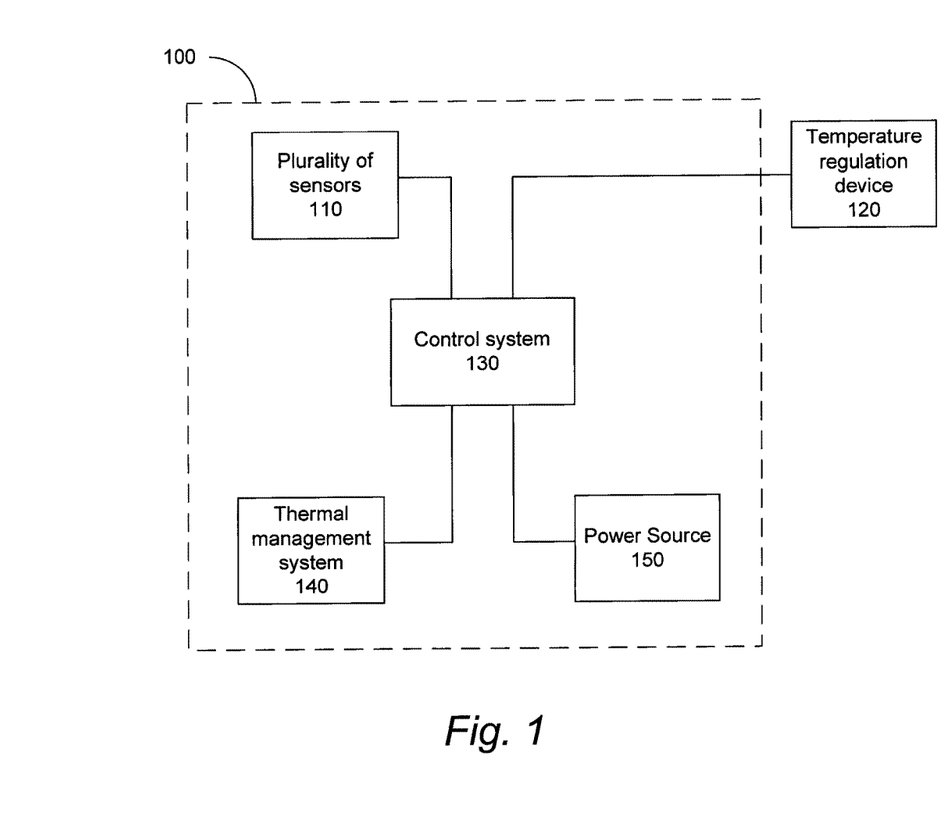
FIG. 1 depicts an exemplary overview of the temperature regulation system.

FIG. 1 depicts an artificial hypothalamus system, hereby referred to as temperature regulation system 100, configured to regulate the temperature of a patient as further described herein. The temperature regulation system 100 can include a plurality of sensors 110, a control system 130, a thermal management system 140, and a power source 150. The temperature regulation system 100 can be communicably coupled to a temperature regulation device 120, such that the temperature regulation system 100 can be integrated into any temperature regulation device 120.

The plurality of sensors 110 can provide various sensor output to the control system 130, as further described herein.

The temperature regulation device 120 can be any device configured to regulate a temperature of a human, for example. The temperature regulation device 120 can regulate temperature with external water circulation, such as the Blanketrol II, external air circulation, such as the Caircooler CC1000, external water circulation using self-adhesive gel-coated pads, such as the Arctic Sun, and/or intravascular heat exchange, such as Icy-catheter, for example. It should be appreciated that the temperature regulation system 100 can be integrated into any temperature regulation device 120.

The control system 130 can communicably couple the plurality of sensors 110, the temperature regulation device 120, the thermal management system 140, and the power source 150.

The thermal management system 140 can activate various temperature adjustment mechanisms to predetermined levels of output based on signals from the control system 130, thereby changing the temperature of the human in order to regulate the temperature of the human, as further described herein. It should be appreciated that the temperature adjustment mechanism may be mechanisms previously incorporated into the temperature regulation device 120, or may be originally part of the temperature regulation system 100.

The power source 150 can provide power to the temperature regulation system 100. Optionally, or additionally, the power source 150 can provide power to the temperature regulation device 120.

Figure 2:
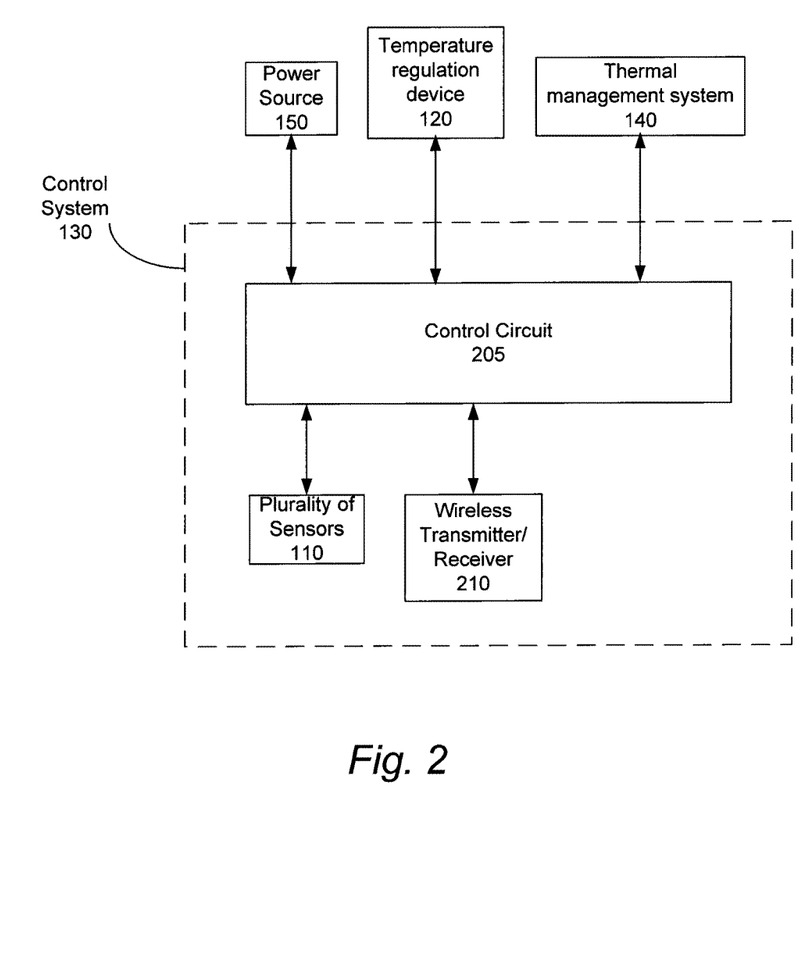
FIG. 2 depicts an exemplary overview of the control system for the temperature regulation system.

FIG. 2 depicts the control system 130 of the temperature regulation system 100. The control system 130 can include a control circuit 205 that can be disposed within the temperature regulation system 100. The control circuit 205 can be configured to receive data and/or to monitor, record, store, index, process, and/or communicate such data. The control circuit 205 can include components such as, for example, a memory, a central processing unit (CPU), Input/Output (I/O) devices or any other components that can be used to run an application. The control circuit 205 can be programmed to execute a set of predetermined instructions. Such instructions can be stored in the memory. Various lookup tables, maps, and mathematical equations can also be stored in the memory. However, one skilled in the art will appreciate that such information can be stored on or read from various types of computer-readable media, such as secondary storage devices, including hard disks, floppy disks, optical media, CD-ROM, or other forms of RAM or ROM. Various other known circuits can also be associated with the control circuit 205, such as power supply circuitry, signal-conditioning circuitry, solenoid driver circuitry, communication circuitry, and the like. It should be appreciated that the control circuit 205 can alternatively include multiple controllers, each dedicated to perform one or more of these or other functions. Such multiple controllers can be configured to communicate and cooperate with one another.

The control circuit 205 is communicably coupled to a plurality of sensors 110 of the control system 130. Each of the sensors 110 can be configured to provide signals indicative of parameters related to the current environment of the temperature regulation system 100. The sensors 110 can be disposed at various locations in the temperature regulation system 100.

The control system 130 is also communicably coupled to the temperature regulation device 120, the thermal management system 140, and a wireless receiver/transmitter 210.

The wireless receiver/transmitter 210 can facilitate communications between the control system 130 and the temperature regulation system 100.

The temperature regulation system 100 also includes a power source 150 configured to provide power to the various components of the temperature regulation system 100 including the control system 130, to the temperature regulation device 120, the thermal management system 140, and the wireless receiver/transmitter 210. The power source 150 can be disposed within the temperature regulation system 100. The power source 150 can include one or more rechargeable batteries and/or electrical wiring that can connect to an electrical outlet or a generator, for example, as would be known to one of ordinary skill in the art. In an exemplary embodiment, the control circuit 205 can be configured to regulate a power supplied by the power source 150 to the various components of the temperature regulation system 100. Further, the control circuit 205 can be configured to determine a level of electrical energy stored in the power source 150.

Figure 3:
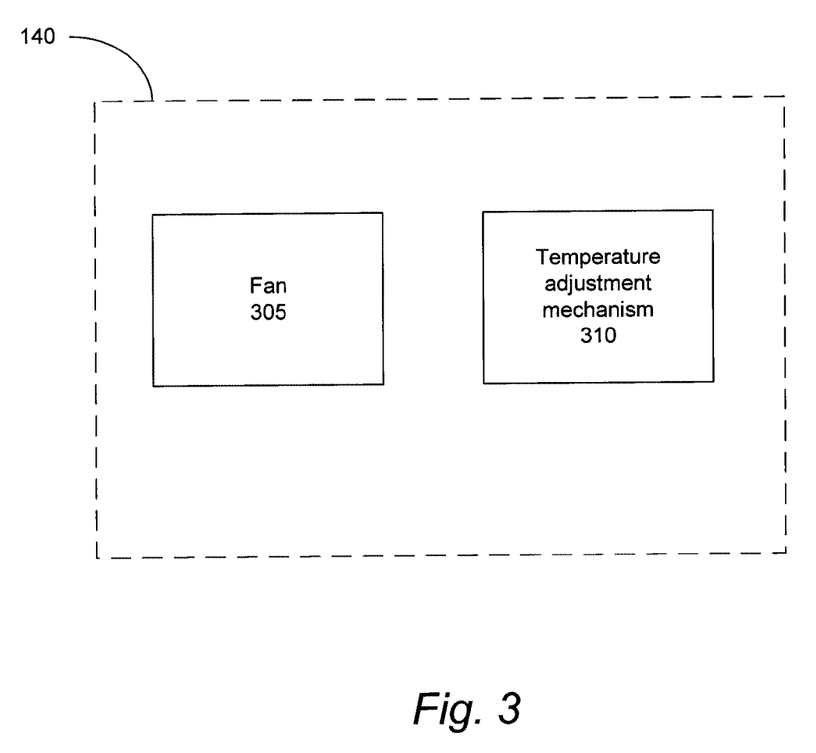
FIG. 3 depicts an exemplary overview of the thermal management system.

FIG. 3 depicts an exemplary overview of the thermal management system 140. The thermal management system 140 can include a fan 305 and a temperature adjustment mechanism 310. The fan 305 can blow air to change the temperature of the human. For example, cold water can be sprayed on the human and the fan can blow hot air to create evaporation, as would be known to one of ordinary skill in the art.

The temperature adjustment mechanism 310 can change the temperature of the human in order to regulate the temperature of the human. For example, the temperature adjustment mechanism 310 can be a cooling blanket, a water circulation device, an intravascular heat exchange system, and the like. It should be appreciated that the temperature adjustment mechanism 310 can be the temperature regulation device 120, such that the temperature regulation device 120 can be part of the thermal management system 140.

Figure 4:
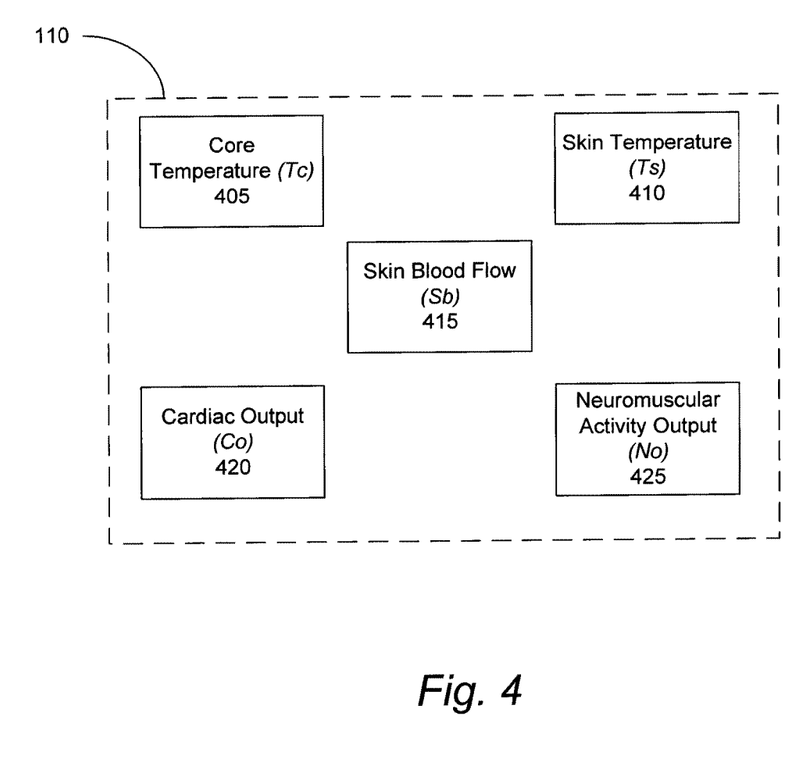
FIG. 4 depicts an exemplary overview of the plurality of sensors.

FIG. 4 depicts an exemplary overview of the plurality of sensors 110. The plurality of sensors 110 includes a core temperature (Tc) sensor 405, a skin temperature (Ts) sensor 410, a skin blood flow (Sb) sensor 415, a cardiac output (Co) sensor 420, and a neuromuscular activity output (No) sensor 425. Each sensor can be disposed at a predetermined location on a human, for example, to monitor various outputs, such that each sensor can monitor a predetermined type of output. For example, the core temperature sensor 405 can be a thermometer used to measure core temperature, the skin temperature sensor 410 can be a thermocouple to measure skin temperature through the thermoelectric effect, the skin blood flow sensor 415 can be an ultrasonic flow meter that measures the velocity of a fluid using ultrasound, the cardiac output sensor 420 can be an echocardiogram to calculate cardiac output, and the neuromuscular activity output sensor 425 can be an acceleromyograph to measure the force produced by a muscle after it has undergone nerve stimulation. It should be appreciated that other sensors may be able to perform the measurements of the core and skin temperature, the skin blood flow, the cardiac output, and the neuromuscular activity output, and the sensors described herein are not intended to be limiting.

Figure 5:
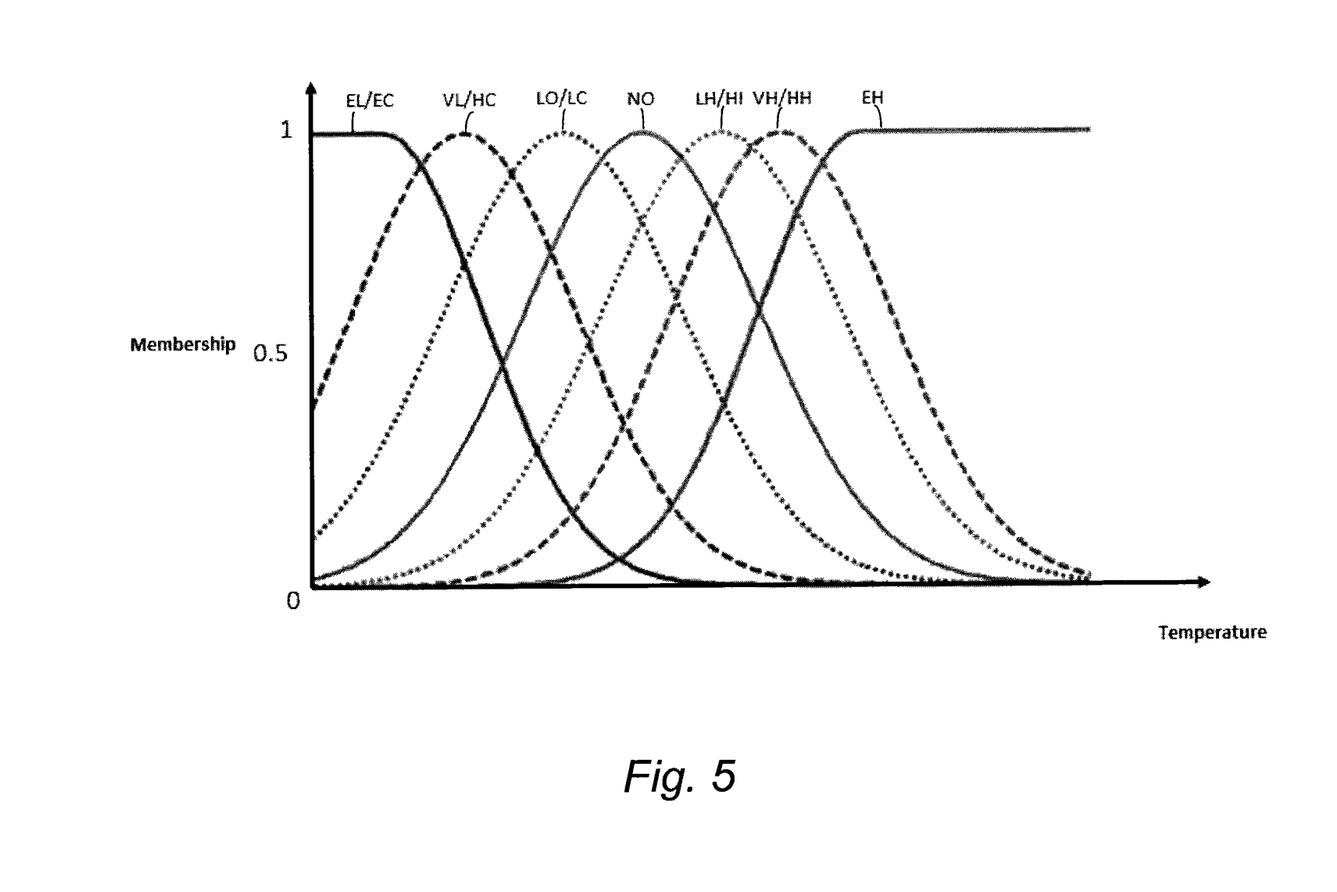
FIG. 5 depicts an exemplary overview of the membership functions for input variables.

FIG. 5 depicts an exemplary overview of the membership functions for input variables. FIG. 5 illustrates a Gaussian representation of the input variables for core temperature (Tc) 405 and skin temperature (Ts) 410. Membership is evaluated on the y-axis from 0 to 1, and the x-axis corresponds to a range of predetermined temperature values. It should be appreciated that membership functions for input variables other than temperature may be represented using other functions such as Sigmoid, S-shape, Trapezoid, Triangular, or a custom defined function as would be known to one of ordinary skill in the art. Further, the x-axis can be set to correspond to any predetermined range of input values.

The membership functions can be evaluated using information from a table of linguistic variables corresponding to each input, and a table of exemplary fuzzy rules, as described herein.

Table 1 can be a table of linguistic variables corresponding to each input, the input being a value corresponding to the output of one of the plurality of sensors 110.

TABLE 1

| Tc | Ts | Sb | Co | No |
|---|---|---|---|---|
| Extreme Heat (EH) | Extreme Heat (EH) | Extreme High (EH) | Extreme High (EH) | Extreme High (EH) |
| High Heat (HH) | High Heat (HH) | Very High (VH) | Very High (VH) | Very High (VH) |
| Light Heat (LH) | Light Heat (LH) | High (HI) | High (HI) | High (HI) |
| Normal (NO) | Normal (NO) | Normal (NO) | Normal (NO) | Normal (NO) |
| Light Cold (LC) | Light Cold (LC) | Low (LO) | Low (LO) | Low (LO) |
| High Cold (HC) | High Cold (HC) | Very Low (VL) | Very Low (VL) | Very Low (VL) |
| Extreme Cold (EC) | Extreme Cold (EC) | Extreme Low (EL) | Extreme Low (EL) | Extreme Low (EL) |

It should be appreciated that any abbreviation can be used as a predetermined identifier and the abbreviations included herein are not intended to be the only possible identifiers for any specific values.

It should further be appreciated that EL/EC is intended to represent "Extremely Low" or "Extremely Cold", respectively, and is illustrated as such simply to capture grammatical discrepancies as one might not say cardiac output (Co) is "Extremely Cold", but would rather more accurately describe cardiac output as "Extremely Low", for example. Therefore, it should be appreciated that EL/EC can equally represent the corresponding membership function, and the same can apply to VL/HC, LO/LC, LH/HI, and VH/HH as seen in Table 1.

Additionally, Table 2 can be a table of exemplary fuzzy rules where To refers to output temperature for the temperature adjustment mechanism 310, and Sp refers to fan speed for the fan 305. The fuzzy rules can be used to evaluate the relationship between the linguistic variables, such that the linguistic variables evaluated in each fuzzy rule are determined by evaluating the membership functions in FIG. 5. For example, a predetermined temperature can be used as an input corresponding to a point on the x-axis. The predetermined temperature can be used to evaluate a level of membership (y-axis) for each membership function.

TABLE 2

| Rule | Tc | | Ts | | Sb | | Co | | No | then | To | and | Sp |
|---|---|---|---|---|---|---|---|---|---|---|---|---|---|
| 1 | If EC | and | EC | and | VL | and | VL | and | VH | then | VH | and | VH |
| 2 | If EC | and | EC | and | VL | or | VL | or | VH | then | HI | and | VH |
| 3 | If EC | and | LC | and | NO | and | NO | and | LO | then | HI | and | NO |
| ... | ... | ... | ... | ... | ... | ... | ... | ... | ... | ... | ... | ... | ... |

It should be appreciated that more fuzzy rules can be added to create a more robust fuzzy rule set, as would be known to one of ordinary skill in the art. Rules 1-3 are intended to be the start of a fuzzy rule set such that the fuzzy rules can be used to evaluate a broader range of results from the evaluation of the membership functions.

It should also be appreciated that there may be output signals other than output temperature (To) and fan speed (Sp) used to regulate temperature. For example, cold water circulation could be a mechanism for temperature regulation and would have additional parameters including water temperature and water speed.

Figure 6:
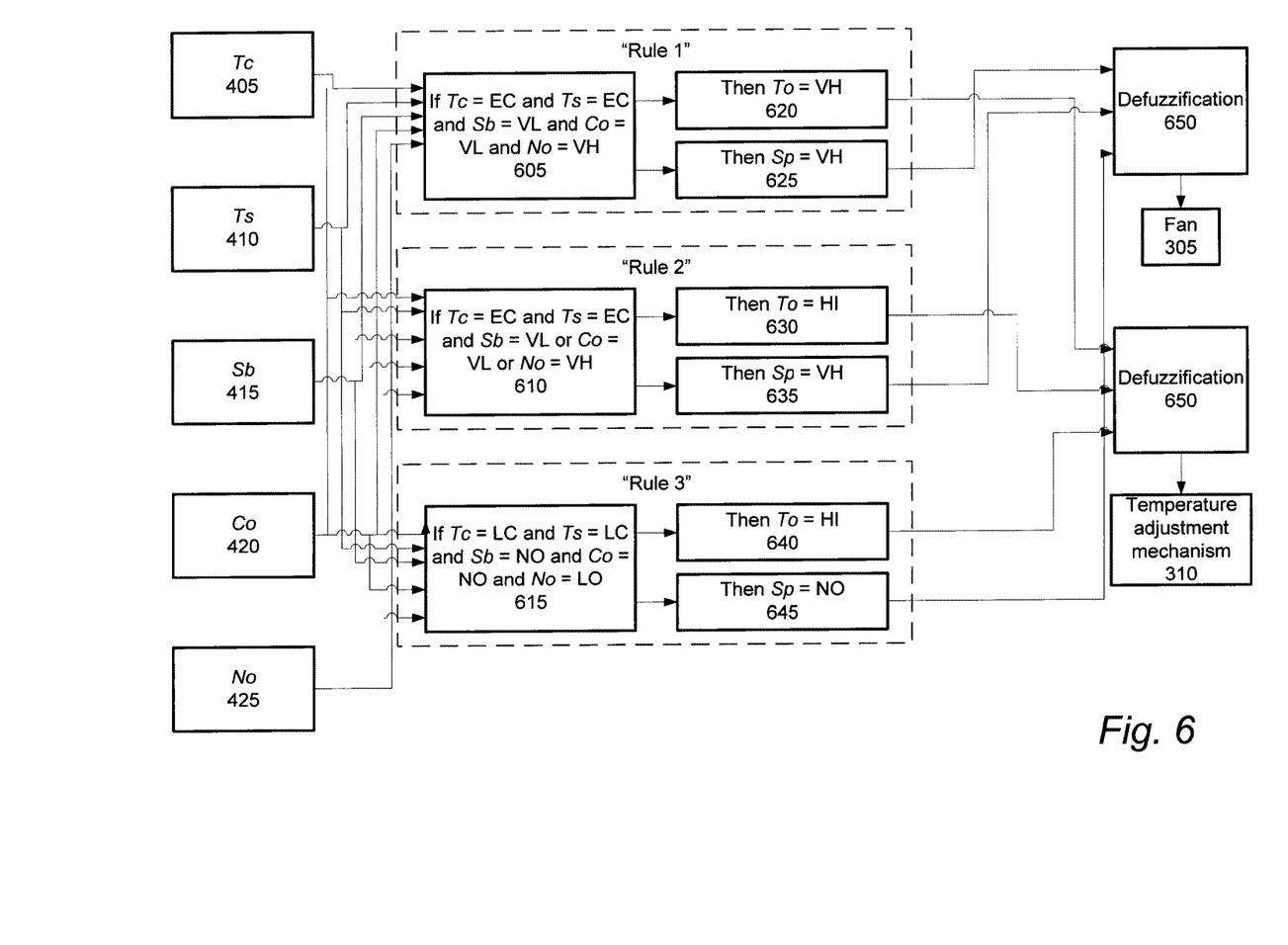
FIG. 6 depicts an exemplary overview of the Fuzzy Logic System.

FIG. 6 depicts an exemplary overview of a Fuzzy Logic System using fuzzy logic rules. The control system 130, via processing circuitry, can utilize the Fuzzy Logic System to determine optimal cooling, thereby determining the appropriate output for the thermal management system 140. The fuzzy logic rules depicted in FIG. 6 are Rule 1, Rule 2, and Rule 3 from Table 2. The Fuzzy Logic System can map the non-linear input datasets to predetermined output states. For example, the temperature regulation system 100 can act as a regulator to regulate body temperature according to pre-defined membership functions. The Fuzzy Logic System can include initialization, where initialization can include defining linguistic variables (Table 1), constructing membership functions (FIG. 5), and constructing a rule base (Table 2). Next, the Fuzzy Logic System can include fuzzification, where fuzzification can be converting input data to fuzzy values by evaluating the membership functions. Further, the Fuzzy Logic System can include inference, where inference can include evaluating the fuzzy rules. Finally, the Fuzzy Logic System can include defuzzification, where defuzzification can be converting one or more consequents of the fuzzy rules to non-fuzzy values. The non-fuzzy values can be precise values corresponding to a precise power output for the fan 305, for example.

A Rule 1 antecedent 605 can receive sensor output from Tc 405, Tc 410, Sb 415, Co 420, and No 425. The Rule 1 antecedent 605 can be evaluated to determine a first Rule 1 consequent 620 and a second Rule 1 consequent 625 following the corresponding Rule 1 from Table 2. Similarly, a Rule 2 antecedent 610 can receiver sensor output, and the Rule 2 antecedent 610 can be evaluated to determine a first Rule 2 consequent 630 and second Rule 2 consequent 635. Additionally, following the same steps as Rule 1 and Rule 2, a Rule 3 antecedent 615 can receive sensor output, and the Rule 3 antecedent 615 can be evaluated to determine a first Rule 3 consequent 640 and a second Rule 3 consequent 645.

The first Rule 1 consequent 620, the first Rule 2 consequent 630, and the first Rule 3 consequent 640 can be combined for defuzzification 650. The defuzzification 650 can be the centroid method, for example, which can determine a precise output value based on the consequents. For example, the first Rule 1 consequent 620, the first Rule 2 consequent 630, and the first Rule 3 consequent 640 can correspond to output temperatures (To) for the temperature adjustment mechanism 310 of VH, HI, and HI, respectively. The results, VH, HI, and HI, can be evaluated using the centroid method, for example, as would be known to one of ordinary skill in the art, to determine a precise weighted value for the output temperature (To) for the temperature adjustment mechanism 310.

It should be appreciated that the defuzzification 650 is not limited to the centroid method. For example, defuzzification 650 can include a bisector of area method, a middle of maximum method, a least of maximum method, a first of maximum method, and the like.

Similarly, a precise weighted value for the fan speed (Sp) for the fan 305 can be determined through the centroid method, for example, using the second Rule 1 consequent 625, the second Rule 2 consequent 635, and the second Rule 3 consequent 645.

Figure 7:
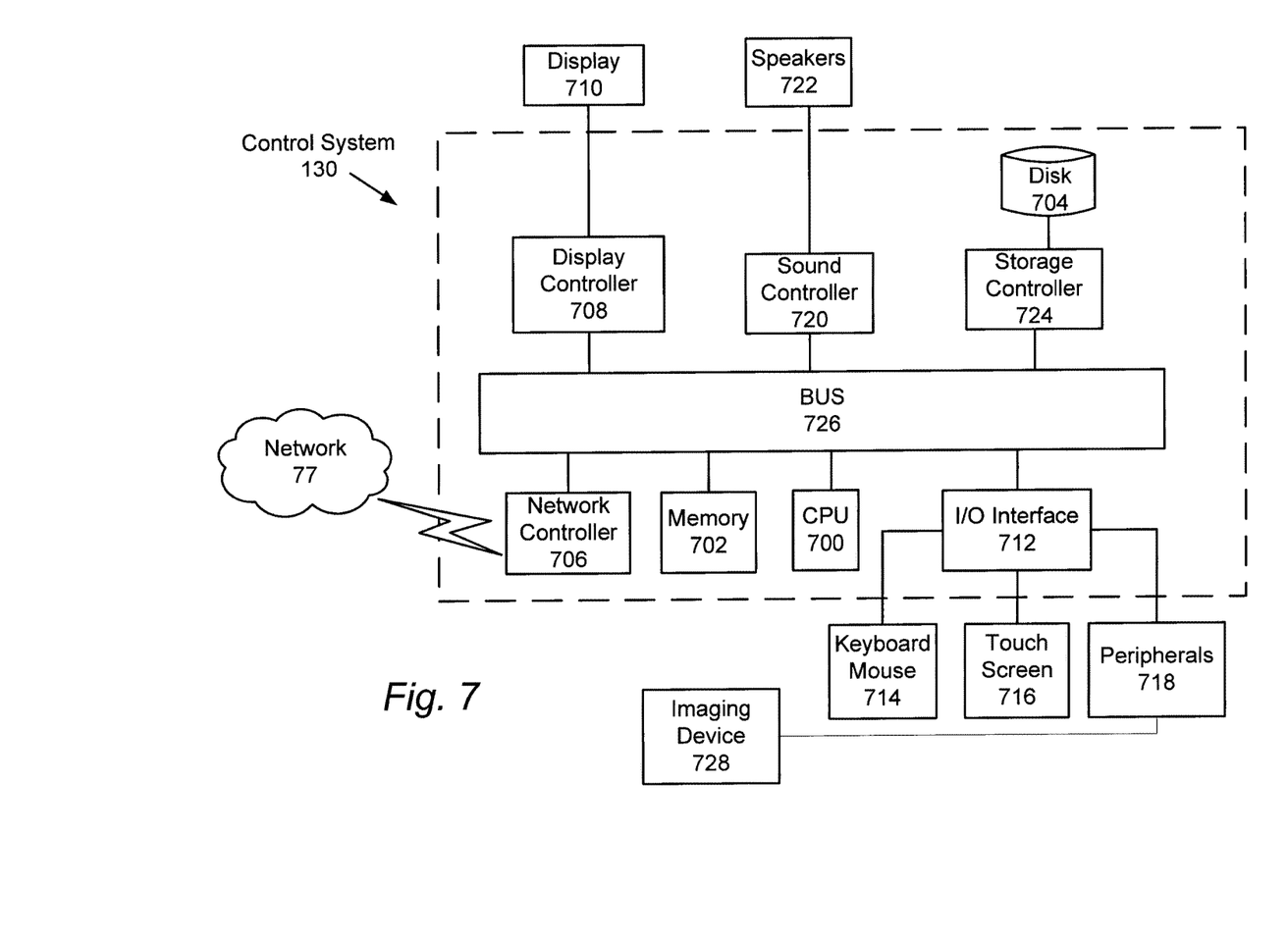
FIG. 7 depicts an exemplary hardware description for the control system.

Next, a hardware description of the control system 130 according to exemplary embodiments is described with reference to FIG. 7. In FIG. 7, the control system 130 includes a CPU 700 which performs the processes described herein. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the control system 130 communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to achieve the control system 130 may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The control system 130 in FIG. 7 also includes a network controller 706, such as an Intel Ethernet PRO network interface card from Intel Corporation of America, for interfacing with network 77. As can be appreciated, the network 77 can be a public network, such as the Internet, or a private network such as an LAN or WAN network, or any combination thereof and can also include PSTN or ISDN sub-networks. The network 77 can also be wired, such as an Ethernet network, or can be wireless such as a cellular network including EDGE, 3G and 4G wireless cellular systems. The wireless network can also be WiFi, Bluetooth, or any other wireless form of communication that is known.

The control system 130 further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the control system 130, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the control system 130. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

Figure 8:
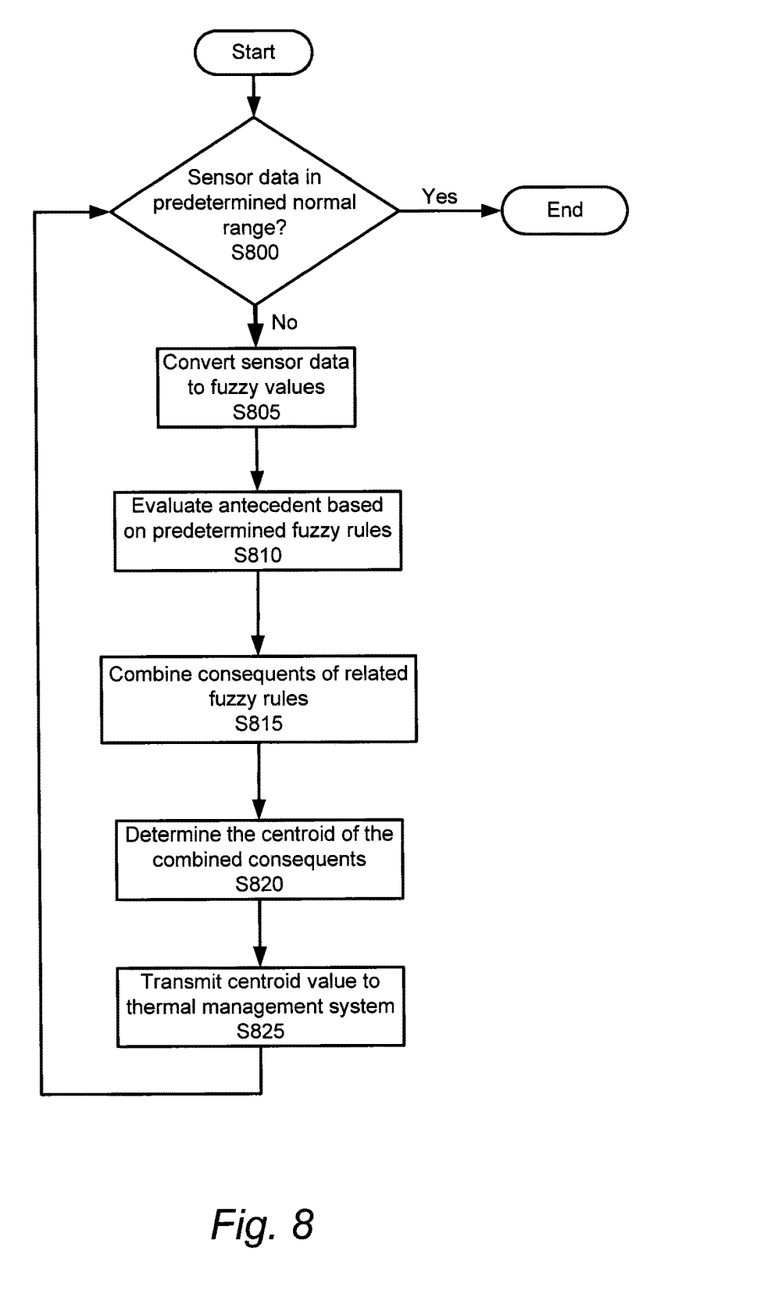
FIG. 8 is a flowchart depicting an exemplary method of regulating temperature for a human.

Next, FIG. 8 illustrates an exemplary algorithmic flowchart for regulating the temperature of a human in real time according to one aspect of the present disclosure. The hardware description herein, exemplified by the structure example shown in FIG. 7 constitutes or includes specialized corresponding structure that is programmed or configured to perform the algorithm shown in FIG. 8. For example, the algorithm shown in FIG. 8 may be performed by the circuitry included in the single device shown in FIG. 7, or the algorithm may be performed in a shared manner distributed over the circuitry of any plurality of device.

In S800, it can be determined if the sensor data from the plurality of sensors 110 is within a predetermined normal range. For example, the core temperature (Tc) sensor 405 might say 98.6° F., which would be considered a normal core body temperature. Alternatively, the core temperature (Tc) sensor 405 might say 103° F. which is widely accepted as not being within a normal range for core body temperature. The sensor data can be monitored continuously as part of a feedback loop. If the sensor data from the plurality of sensors 110 is within a normal range, then the process can end. However, if the sensor data from the plurality of sensors 110 is not within a normal range, then the sensor data can be converted to fuzzy values in S805.

In S805, the sensor data can be converted to fuzzy values (fuzzification) using the membership functions depicted in FIG. 5, for example. The precise sensor data can be converted to fuzzy values by determining the degree of membership for which the sensor data belongs to each membership function.

In S810, the fuzzy values can be evaluated using predetermined fuzzy rules, such that the fuzzy values are the antecedent of the fuzzy rules. The consequent of the fuzzy rules can be determined based on the evaluation of the antecedent. In other words, it can be determined to what degree of membership do the fuzzy values belong to all the conditions in the antecedent.

In S815, the related consequents from all the fuzzy rules can be combined, as depicted in the defuzzification 650 in FIG. 6. Each consequent can correspond to a degree of membership in an output function, as would be known to one of ordinary skill in the art, such that the combination of the consequents results in a fuzzy set. The fuzzy set can be the combination of the restricted membership functions, such that the restricted membership functions are the membership functions evaluated to a degree of membership based on the consequents of the fuzzy rules.

In S820, the combined consequents can be evaluated using the centroid method to determine a centroid of the restricted membership functions. The centroid method can be used to determine a center of mass, as would be known by one of ordinary skill in the art, to produce a precise weighted value.

In S825, the centroid value can be transmitted to the thermal management system 140. The centroid value can be used by the thermal management system 140 to activate the fan 305, for example, to a specific power output that corresponds to a specific fan speed. After the centroid value is transmitted to the thermal management system 140, the process can return to S800 to continue a feedback loop providing real time temperature regulation for a human until the sensor data is in a predetermined normal range.

In one or more embodiments of the disclosed subject matter, the plurality of sensors 110 can include an electromyography sensor, a vibration sensor (e.g., accelerometer), and an imaging device 728 as illustrated in FIG. 7. The electromyography sensor (EMG) can measure the electrical signals of muscle activity, which can detect shivering, for example. Similarly, the vibration sensor can detect a mechanical response of the human shivering by detecting movement of the human. Additionally, the imaging device 728 can detect visible tremors that may be associated with shivering. The imaging device 728 may be used individually or in combination with one or more of the electromyography sensor and the vibration sensor. The electromyography sensor, the vibration sensor, and the imaging device can be used to identify shivering and send a signal to the control system 130 to adjust the thermal management system 140 accordingly to prevent shivering, skin vasoconstriction, and the like while continuing to cool the human as quickly as possible to prevent irreversible damage or death.

In one or more embodiments of the disclosed subject matter, the input for the thermal management system 140 can be a predetermined illness (post-cardiac arrest) or condition (e.g., measles, chicken pox, staph infection, etc.) enter by a physician, for example. The illness or condition can correspond to a predetermined cooling profile. Before a final diagnosis can occur confirming the illness or condition, the physician can enter a plurality of potential illnesses or conditions a patient may have, and the control system 130 can combine the predetermined cooling profiles, using the centroid method, for example, until a final confirmed diagnosis can be made by the physician. Therefore, the temperature regulation system 100 can operate by treating an illness and/or condition rather than treating one or more symptoms.

Figure 9:
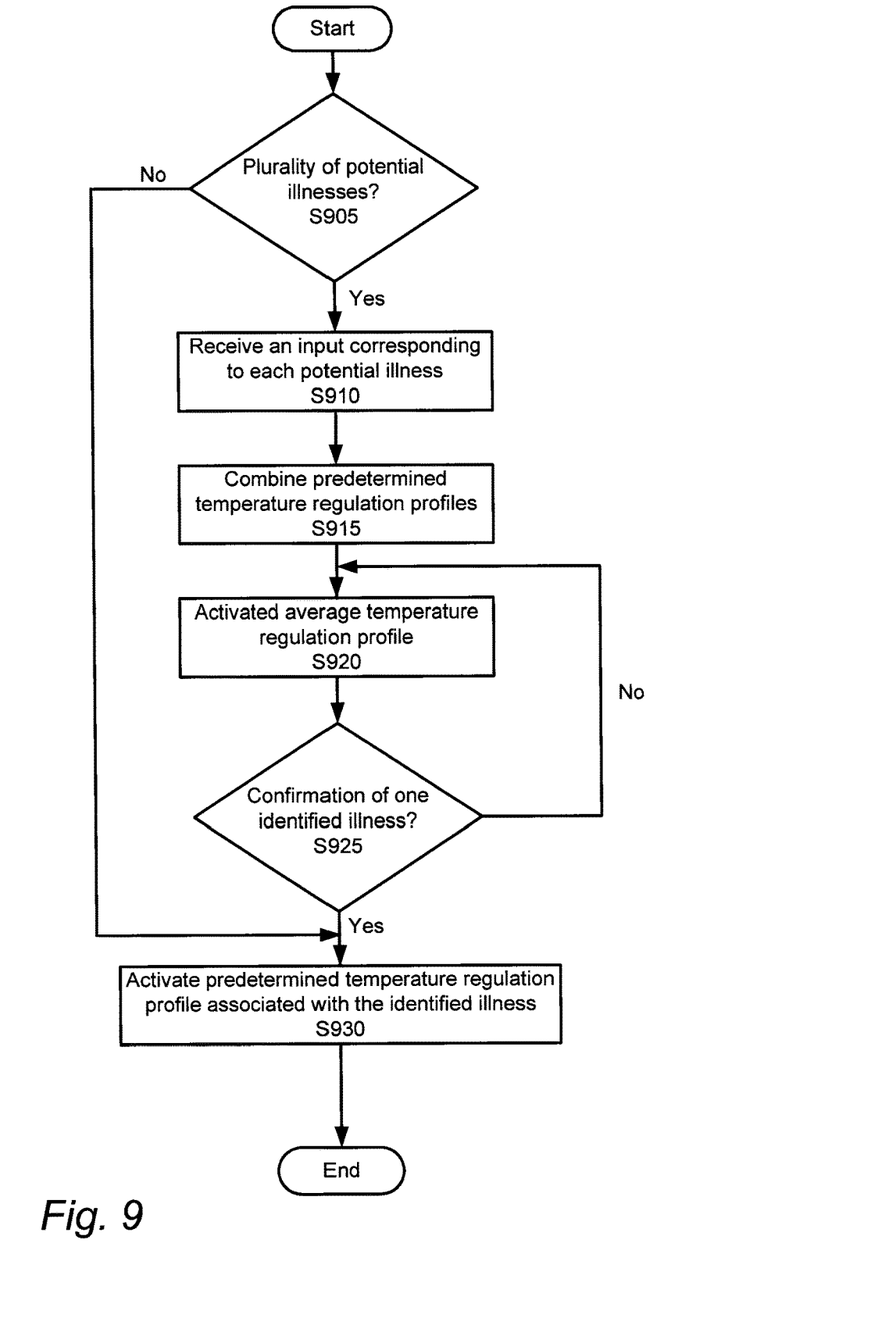
FIG. 9 is a flowchart depicting an exemplary method of determining optimal temperature regulation by identifying an illness.

Next, FIG. 9 illustrates an exemplary algorithmic flowchart for determining a temperature regulation profile based on a plurality of potential illnesses.

In S905, it can be determined if there are a plurality of potential conditions and/or illness as determined by a physician with respect to a patient, for example. If there is not a plurality of illnesses, the process can continue to S930 to activate a predetermined temperature regulation profile associated with that identified condition and/or illness. However, if a single condition and/or illness of the patient cannot be identified by the physician, then an input corresponding to each potential illness can be received in S910.

In S910, the physician can input each of the plurality of potential illnesses before the physician has time to determine the final diagnosis. In many cases, it may be beneficial to begin temperature regulation immediately before the physician can take the time to fully diagnose the patient with one condition and/or illness. Therefore, each condition and/or illness can have an associated temperature regulation profile. The temperature regulation profile associated with a specific condition and/or illness may have been determined by averaging all the temperature regulation profiles, as determined in response to the plurality of sensors 110, of patients with the same condition and/or illness. After each potential illness has been received, the temperature regulation profiles can be combined in S915.

In S915, the temperature regulation profiles corresponding to each of the received conditions and/or illnesses can be combined. An average temperature regulation profile, wherein the average temperature regulation profile is a predetermined combination of the temperature regulation profiles associated with each condition and/or illness, can be determined via the centroid method, for example.

In S920, the average temperature regulation profile can be activated to treat the patient.

In S925, it can be determined if one identified illness has been confirmed, or diagnosed, by the physician, for example. If there has not been a confirmed single diagnosis, the process can return to S920 to continue administering the average temperature regulation profile. However, if a single illness has been identified, or diagnosed, the predetermined temperature regulation profile corresponding to the identified illness and/or condition can be activated in S930. Therefore, the patient can be treated in response to the condition and/or illness, rather than the symptoms. After the predetermined temperature regulation profile associated with the single identified condition and/or illness has been activated, the process can end.

An advantage of the temperature regulation system 100 can be to maintain optimal cooling with limited or no adverse effects, wherein the adverse effects can include shivering and skin vasoconstriction. Consequences of these adverse effects can include discomfort, hypertension, and sympathetic nervous system activation. The temperature regulation system 100 can eliminate or significantly reduce the adverse effects, improve blood flow, and therefore improve temperature regulation efficiency and patient comfort through real time temperature regulation.

More specifically, an advantage is to create an artificial hypothalamus via system 100. For example, when the cooling process begins, such as using ice on the skin or a cooling blanket (via temperature adjustment mechanism 310, for example), the skin can be cooled rapidly. However, when skin temperature has decreased below 32° C. to 33° C., thermoreceptors in the patient send signals to the hypothalamus, thereby causing vasoconstriction and shivering which stops the cooling effect and creates a paradoxical response which maintains high core temperature. The one or more embodiments disclosed herein, via the artificial hypothalamus, can monitor skin temperature, circulation, muscle activity, and the like to maintain skin temperature at 32° C. to 33° C. to prevent adverse effects including vasoconstrictions and shivering, thereby maintaining efficient, predictable, and well tolerated temperature regulation.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

What is claimed is:

1. An artificial hypothalamus system comprising:
a plurality of sensors;
a thermal management system configured to apply optimal temperature regulation via one or more of a fan and a temperature adjustment mechanism; and
a control system, communicably coupled to the plurality of sensors, and the thermal management system, wherein circuitry of the control system is configured to
determine if sensor data from the plurality of sensors is in a predetermined normal range,
convert the sensor data to fuzzy values when the sensor data is not in the predetermined normal range,
combine one or more related consequents of the predetermined fuzzy rules, wherein the consequent is determined based on the evaluation of an antecedent,
evaluate the combined consequents to determine a centroid value using a centroid method, and
transmit the centroid value to the thermal management system to activate the thermal management system to a predetermined activation level based on the centroid value.

2. The artificial hypothalamus system according to claim 1, wherein the sensor data includes data from a plurality of sensors including a core temperature sensor, a skin temperature sensor, a skin blood flow sensor, a cardiac output sensor, and a neuromuscular activity output sensor.

3. The artificial hypothalamus system according to claim 2, wherein the plurality of sensors includes an electromyography sensor, a vibration sensor, and an imaging device.

4. The artificial hypothalamus system according to claim 3, wherein the imaging device is configured to detect visible movement associated with shivering via image recognition software.

5. The artificial hypothalamus system according to claim 4, wherein the imaging device is configured to detect shivering in combination with one or more of the electromyography sensor and the vibration sensor.

6. The artificial hypothalamus system according to claim 1, wherein the sensor data from the plurality of sensors and any indication of shivering via the imaging device is monitored continuously as part of a feedback loop.

7. The artificial hypothalamus system according to claim 6, wherein the circuitry is configured to optimize temperature regulation in real time via the feedback loop.

8. The artificial hypothalamus system according to claim 7, wherein the optimal temperature regulation via the feedback loop prevents shivering and skin vasoconstriction.

9. The artificial hypothalamus system according to claim 1, wherein the circuitry is configured to
determine if a plurality of predetermined temperature regulation profiles have been received as input to the control system, wherein each predetermined temperature regulation profile is associated with an identified potential illness,
combine the plurality of predetermined temperature regulation profiles to create an average predetermined temperature regulation profile when the control system receives a plurality of predetermined temperature regulation profiles as input,
activate the average predetermined temperature regulation profile,
determine if a single illness has been identified, and
activate the predetermined temperature regulation profile corresponding to the single identified illness when the single illness has been identified.

10. A method of regulating temperature comprising:
determining, via processing circuitry, if sensor data from a plurality of sensors is in a predetermined normal range;

converting the sensor data to fuzzy values when the sensor data is not in the predetermined normal range;

combining one or more related consequents of the predetermined fuzzy rules;

evaluating the combined consequents to determine a centroid value using a centroid method;

transmitting the centroid value to a thermal management system to activate the thermal management system to a predetermined activation level based on the centroid value.

11. The method of claim 10, wherein the sensor data includes data from a plurality of sensors including a core temperature sensor, a skin temperature sensor, a skin blood flow sensor, a cardiac output sensor, a neuromuscular activity output sensor, an electromyography sensor, a vibration sensor, and an imaging device.

12. The method of claim 11, further comprising:
detecting visible movement associated with shivering via the imaging device.

13. The method of claim 12, further comprising:
detecting shivering independently via the imaging device, or in combination with one or more of the electromyography sensor and the vibration sensor.

14. The method of claim 13, further comprising:
monitoring continuously the sensor data from the plurality of sensors and any indication of shivering from the imaging device as part of a feedback loop.

15. The method of claim 14, further comprising:
optimizing temperature regulation to prevent shivering and skin vasoconstriction via the feedback loop.

16. The method of claim 10, further comprising:
determining, via processing circuitry, if a plurality of predetermined temperature regulation profiles have been received as input to the control system, wherein each predetermined temperature regulation profile is associated with an identified potential illness;

combining the plurality of predetermined temperature regulation profiles to create an average predetermined temperature regulation profile when the control system receives a plurality of predetermined temperature regulation profiles as input, activating the average predetermined temperature regulation profile;

determining, via processing circuitry, if a single illness has been identified; and activating the predetermined temperature regulation profile corresponding to the single identified illness when the single illness has been identified.

17. An artificial hypothalamus system comprising:
a temperature regulation device;
a plurality of sensors;
a thermal management system; and
a control system communicably coupled to the temperature regulation device, the plurality of sensors, and the thermal management system, wherein the control system circuitry is configured to
determine if sensor data from the plurality of sensors is in a predetermined normal range,
convert the sensor data to fuzzy values when the sensor data is not in the predetermined normal range,
combine one or more related consequents of the predetermined fuzzy rules, wherein the consequent is determined based on the evaluation of an antecedent,
evaluate the combined consequents to determine a centroid value using a centroid method, and
transmit the centroid value to the thermal management system to activate the thermal management system to a predetermined activation level based on the centroid value.

18. The artificial hypothalamus system according to claim 17, wherein the sensor data includes data from a plurality of sensors including a core temperature sensor, a skin temperature sensor, a skin blood flow sensor, a cardiac output sensor, a neuromuscular activity output sensor, an electromyography sensor, a vibration sensor, and an imaging device.

19. The artificial hypothalamus system according to claim 18, wherein the sensor data from the plurality of sensors and any indication of shivering via the imaging device is monitored continuously as part of a feedback loop.

20. The artificial hypothalamus system according to claim 19, wherein the circuitry is configured to optimize temperature regulation in real time via the feedback loop to prevent shivering.

* * * * *